United States Patent
Baccelli

(10) Patent No.: US 6,309,389 B1
(45) Date of Patent: Oct. 30, 2001

(54) RING FOR AN ANGULATION OSTEOSYNTHESIS DEVICE AND OSTEOSYNTHESIS DEVICE INCORPORATING SAME

(75) Inventor: Christian Baccelli, Saint Medard d'Eyrans (FR)

(73) Assignee: Stryker France, S.A. (FR)

( * ) Notice: Subject to any disclaimer, the term of this patent is extended or adjusted under 35 U.S.C. 154(b) by 0 days.

(21) Appl. No.: 09/380,385
(22) PCT Filed: Feb. 25, 1998
(86) PCT No.: PCT/FR98/00367
§ 371 Date: Dec. 6, 1999
§ 102(e) Date: Dec. 6, 1999
(87) PCT Pub. No.: WO98/37824
PCT Pub. Date: Sep. 3, 1998

(30) Foreign Application Priority Data

Feb. 26, 1997 (FR) .................................................. 97 02298

(51) Int. Cl.$^7$ .................................................. A61B 17/56
(52) U.S. Cl. .................................................. 606/61
(58) Field of Search ................................. 606/53, 54, 56, 606/59, 60, 61, 72

(56) References Cited

U.S. PATENT DOCUMENTS 4,065,221 * 12/1977 Cawthorne .......................... 403/284
4,127,119 * 11/1978 Kronner .................................. 606/56
5,176,680 * 1/1993 Vignaud et al. ........................ 606/61
5,242,445 9/1993 Ashman .
5,584,833 * 12/1996 Fournet-Fayard et al. ............ 606/61

FOREIGN PATENT DOCUMENTS

| 487895 | 6/1992 | (EP) . |
| 2659546 | 9/1991 | (FR) . |
| 2682280 | 4/1993 | (FR) . |

* cited by examiner

Primary Examiner—Gene Mancene
Assistant Examiner—Eduardo C. Robert
(74) Attorney, Agent, or Firm—Blakely Sokoloff Taylor & Zafman

(57) ABSTRACT

An osteosynthesis device, in particular for the spine. The device has an outer spherical surface and a substantially cylindrical inner surface, designed to receive a rod of the device. A ring has two matching parts (10) each being U-shaped and having a bottom and a pair of branches taking up a fraction of the axial dimension of the bottom. The distance between the branches is about the same as that of the rod diameter, their respective bottoms facing each other enclosing the rod, and their pairs of branches adjacent. The parts jointly define the outer and inner surfaces. The invention is applicable to linkages adjustable at different angles.

9 Claims, 2 Drawing Sheets

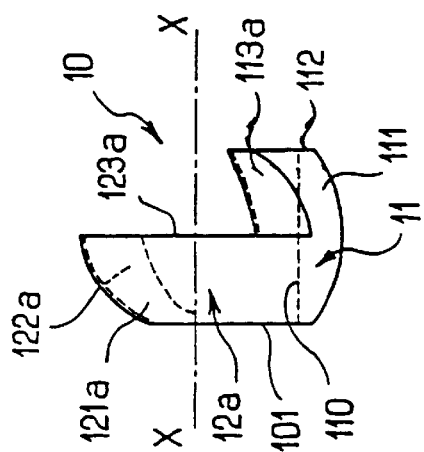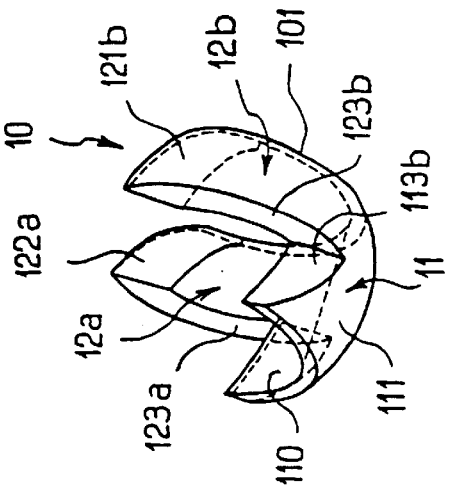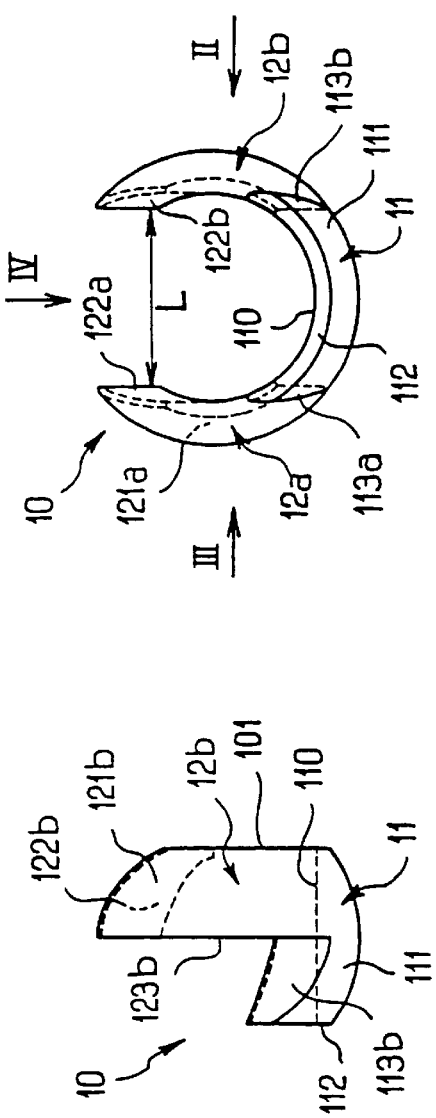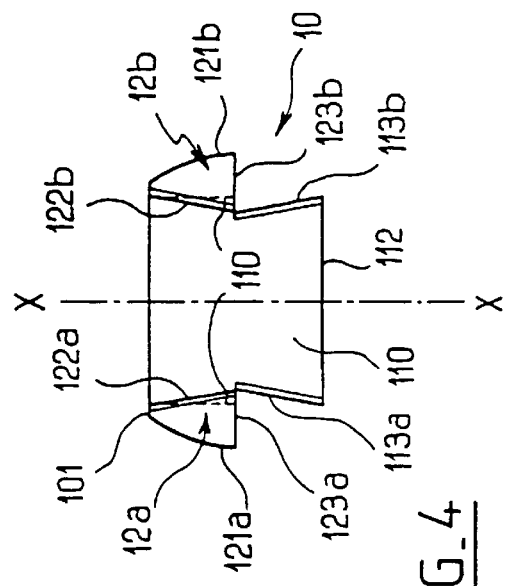

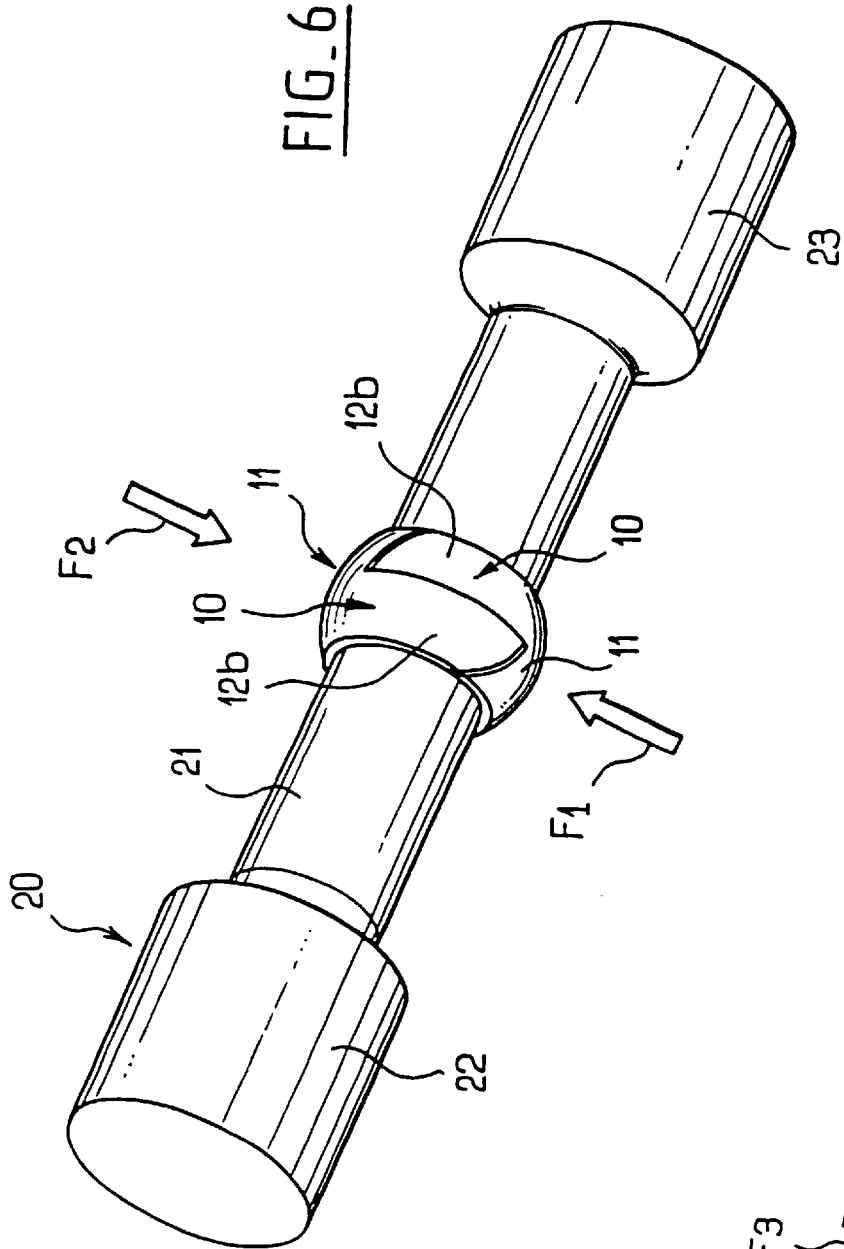
FIG_6
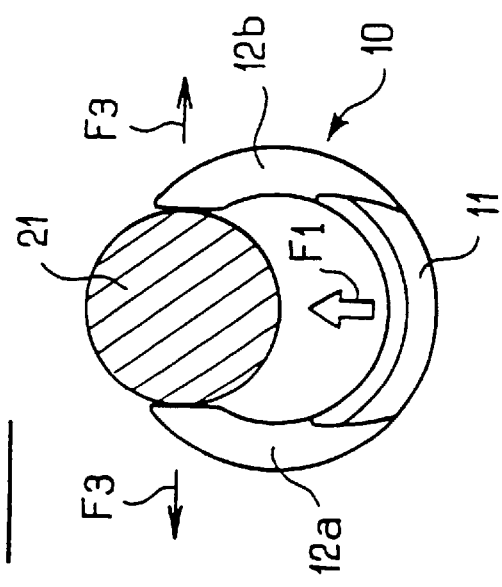
FIG_7

RING FOR AN ANGULATION OSTEOSYNTHESIS DEVICE AND OSTEOSYNTHESIS DEVICE INCORPORATING SAME

FIELD OF THE INVENTION

The present invention relates in general to implants for osteosynthesis, particularly of the spine.

It relates more specifically to a new ring of spherical type intended to allow angular orientation between two components of the implant prior to tightening, and to an implant equipped with such a ring.

BACKGROUND OF THE INVENTION

Document FR-A-2 659 546 discloses a spinal osteosynthesis system which comprises a collection of pedicle screws, each having a spherical seat made in a so-called "forked" head and in which a split ring can be housed. Passing through this ring itself is a rod intended to connect the various screws together, and the ring offers a possibility of angularly orientating the axis of the pedicle screw and the axis of the rod in one or two planes. Once this angular adjustment has been performed, a threaded cap compresses the ring and locks the assembly firmly in position.

The known ring is made of one single piece, with a spherical outer face, a cylindrical inner face with symmetry of revolution, and a slot directed radially and extending between the inner and outer faces.

This slot gives the ring the required deformability so that when clamped into the seat in the pedicle screw using an appropriate threaded member, it can be compressed firmly against the rod, so that once the angular adjustment has been performed, the assembly is held perfectly immobilized.

This known ring does, however, have a limitation: when preparing the implant system prior to or during fitting, it is necessary to slip as many split rings as are needed over the rod from one of its ends.

This is because the deformability of the ring which is afforded by its slot is far from sufficient to allow this slot to be parted temporarily to allow the rod to be introduced radially into the cylindrical passage through the ring. Thus, the practitioner attempting to proceed in this manner would inevitably cause breakage or significant damage to the mechanical qualities or the shape of the ring.

The use of this kind of known ring is therefore restricted to scenarios in which the rod is accessible from at least one of its ends.

SUMMARY OF INVENTION

The present invention aims to alleviate this drawback of the state of the art and to propose a new deformable ring which can be fitted onto a rod even when the latter has neither end free for the said ring to be slipped over it.

Thus the present invention proposes an angular orientation ring for an osteosynthesis device, particularly for the spine, of the type comprising an essentially spherical outer face and an essentially cylindrical inner face intended to take a rod of the device, the ring being characterized in that it is made in two mating parts, each part being substantially U-shaped with a bottom and at least one pair of branches occupying a fraction of the axial dimension of the bottom, the distance between the two branches of one same pair being close to the diameter of a rod intended to take the ring, and the two parts being designed to be inserted over the rod from its side in such a way that their respective bottoms come to substantially face each other, enclosing the rod, and such that their pairs of branches come to be side by side, the said two parts therefore jointly defining an essentially spherical outer face and an essentially cylindrical inner face.

Preferred but non-limiting aspects of the ring according to the invention are as follows:

- each part has a pair of branches and each of the said branches occupies substantially half of the axial dimension of the ring.
- each of the said branches has, at its free end, a projecting shape able to be received in an essentially complementary housing provided in the bottom of the other part.
- the projecting shape of each of the branches of one part is defined by the intersection of a spherical contour of the branch with an end face essentially parallel to the axis of the ring and forming an extension of a semi-cylindrical inner surface defined by the bottom of this same part.
- the said end face of each branch extends slightly obliquely with respect to the axis of the ring.
- the two branches are separated from the bottom by two shoulders extending in planes which, with respect to the axis of the ring, have an obliqueness similar to that of the said end faces.
- the branches of each part are delimited, on a face facing towards the branches of the other part, by a plane perpendicular to the axis of the ring.
- the minimum distance between the two branches of one same pair is locally slightly shorter than the diameter of a rod intended to take the said ring.

The invention also proposes an osteosynthesis device, particularly for the spine, comprising a bone fixation part which has an essentially spherical seat, a ring housed in the said seat, an element for clamping the ring into its seat, and a rod passing through an essentially cylindrical passage formed in the ring, characterized in that the rod forms part of a component comprising, at the two ends of the rod, two parts which are wider than the said rod, and in that the ring is made as defined above, its two parts being fitted onto the rod from the side thereof.

BRIEF DESCRIPTION OF THE DRAWINGS

Other aspects, objects and advantages of the present invention will emerge more clearly from reading the following detailed description of a preferred embodiment thereof, given by way of example and made with reference to the appended drawing, in which:

FIG. 1 is a view along the axis of part of the ring according to the present invention, FIG. 2 is a side view in the direction of arrow II of FIG. 1, FIG. 3 is a side view in the direction of arrow III of FIG. 1, FIG. 4 is a view from above in the direction of arrow IV of FIG. 1, FIG. 5 is a perspective view of the part of the ring of FIGS. 1 to 4, FIG. 6 is a perspective view of an osteosynthesis rod on which a ring consisting of two ring parts identical to the one illustrated in FIGS. 1 to 5 has been mounted, and FIG. 7 is a view in transverse section illustrating the mounting of a ring part on an osteo-synthesis rod.

DETAILED DESCRIPTION OF THE PREFERRED EMBODIMENT

With reference first of all to FIGS. 1 to 5, there have been depicted a part intended, together with another, in this particular instance identical, part, to form a ring with an essentially spherical outer surface and an essentially cylindrical inner surface.

This part 10 has, viewed face-on (FIG. 1), the overall shape of a U with a bottom part 11 and two lateral branches 12a, 12b, these three parts being delimited by respective outer surfaces 111, 121a, 121b which belong to a common sphere.

The bottom part 11 extends, in the direction of the axis XX (that is to say horizontally in FIGS. 2 and 3) a dimension equal to the axial length of the ring, while the two branches 12a, 12b are only, in this direction, only about half of this dimension, the bottom and the two branches having a common end face 101 extending perpendicularly to the axis XX of the ring.

The transition between the bottom and the branches occurs, in the direction of the axis XX, at two shoulders or cut surfaces 113a, 113b which, as shown particularly in FIG. 4, extend in slightly re-entrant planes from the outside of the ring towards the inside.

On the opposite side to the common edge 101, the bottom is delimited by an opposite edge 112 extending in a plane perpendicular to the axis XX, while the branches 12a, 12b are delimited by respective opposite edges 123a, 123b extending in another plane perpendicular to the axis XX is located substantially mid-way between the planes bounding the bottom part.

The bottom part 11 has an inner face 110 which is a portion of a cylinder with symmetry of revolution and which, in the region of the inner faces of the two branches 12a, 12b, is extended to essentially form half a cylinder.

In their free-end region, the inner faces of the two branches 12a, 12b have a cut surface 122a, 122b, respectively, which extends essentially in the continuation of the semi-cylindrical wall 111, but with a slight obliqueness, namely a re-entrant orientation from the outside inward. This obliqueness is preferably similar to that of the shoulders 113a, 113b.

The minimum distance L between the two branches perpendicular to the axis XX (see FIG. 1) is chosen to be slightly shorter than the diameter of a rod on which two parts 10 are to be mounted in order together to form a spherical angular-orientation ring.

It will be seen here that this minimum distance L is in the region of the cut surfaces 122a, 122b, while below this restriction, the dimension of the interior space of the part perpendicular to the axis XX is greater than that of the associated rod, by choosing, for the semi-cylindrical wall 110, a diameter which slightly exceeds the diameter of the rod.

By way of example, and for a part 10 made of a material of the titanium alloy type, or material of comparable elasticity, the distance L is preferably about 15% shorter than the diameter of the rod. Furthermore, the diameter of the surface 110 is larger than the diameter of the rod by a sufficient margin that the necessary freedom of sliding can be achieved.

Now, with reference to FIGS. 6 and 7, a spherical ring is produced on a cylindrical rod 21 by inserting a first part 10 over this rod, and more specifically by placing this part in such a way that its interior space opens towards the rod and by exerting radial force in the direction of arrow F1.

The branches 12a, 12b of the part 10 then temporarily part elastically to allow the rod to enter its interior space; once this has been done, the rod 21 is received, with a small amount of clearance, in its semi-cylindrical cradle defined by the wall 110 of the part. The part 10 can then slide freely along the rod, and held captive thereon in that removal of the part can be achieved only with the use of a thin tool, forming a lever.

A second part 10, identical to the first, is then placed on the rod 21 in the same way, but facing in the opposite direction, or head-to-tail with respect to the part already fitted, and by being subjected to a force in the direction of arrow F2, in the opposite direction to arrow F1.

The positioning of the second part with respect to the first at the instant of this fitting is chosen in such a way that the branches 12a, 12b of the second part run alongside the branches 12a, 12b of the first part.

It will be noted here that the end part of each branch, defined by the end parts of the walls 121a, 122a, 123a (or of the walls 121b, 122b, 123b, respectively) is in the form of a point which, at the end of the fitting of the second part 10, becomes wedged in a housing of essentially complementary shape defined by, on the one hand, the outer surface of the rod 21 and, on the other hand, by the face 113a and by the face 123a of the part 10 fitted earlier (or, respectively, by the outer surface of the rod 21 and by the faces 113b and 123b). By symmetry, the same wedging effect is achieved between the points of the branches 12a, 12b of the part 10 fitted earlier and the corresponding housings of the newly-fitted part.

Thus, the rod 21 makes it possible to prevent translational movement of the two parts 10 in a plane perpendicular to its axis, while the aforementioned fourfold wedging effect ensures that the two parts 10 nest snugly together as shown in FIG. 6, without the possibility of coming apart.

In an extremely simple and easy way the two parts 10 thus form a spherical ring which need not be slipped onto the rod from an end, in contrast to what was the case with an ordinary split ring.

Thus, the present invention makes it possible for a rod 21 to be fitted with a spherical ring particularly when the rod belongs to an osteosynthesis element, designated as a whole as 20, where it forms a connection between two broader elements, depicted diagrammatically as 22, 23 in FIG. 6. This osteosynthesis element 20 may, in particular, be a part for connecting with the sacrum.

Once the ring has been fitted on the rod 21, this ring can collaborate with the other components of an implant as described, in particular, in document FR-A-2 659 546, the ring according to the invention replacing the one-piece split ring described in that document. More specifically, the U shape of each part 10 forming the ring according to the invention exhibits the elastic deformability required so that when the ring is compressed by the tightening of the threaded cap of the implant, it firmly locks the rod 21 against any translational movement and against any tilting with respect to the angular orientation given before tightening. Naturally, the invention is just as applicable to other types of implants involving rings.

Of course, the present invention is not in any way restricted to the embodiment described hereinabove and depicted in the drawings.

In particular, provision may be made for each of the parts 10 to comprise several pairs of branches spaced apart, between which the branches of the other part engage.

Furthermore, although the two parts 10 used to form the ring are, in this example, strictly identical, which makes manufacture and handling easier, two differing parts could be envisaged.

What is claimed is:

1. Angular orientation ring for an osteosynthesis device, for a spine, of a type comprising an essentially spherical outer face and an essentially cylindrical inner face intended to take a rod (21) of the device, wherein the ring has two mating parts (10), each part being substantially U-shaped with a bottom (11) and at least one pair of branches (12a, 12b) occupying a fraction of an axial dimension of said bottom, a distance (L) between the said pair of branches being close to the diameter of said rod intended to take the ring, and the two parts being designed to be inserted over the rod in a transverse direction in such a way that their respective bottoms substantially face each other across said enclosed rod, and such that their pairs of branches are side by side, said two parts jointly defining said essentially spherical outer face and said essentially cylindrical inner face.

2. Ring according to claim 1, wherein each part (10) has a pair of branches (12a, 12b) and in that each of the said branches occupies substantially half of an axial dimension of said ring.

3. Ring according to claim 1 or 2, wherein each of the branches (12a, 12b) has, at its free end, a projecting shape able to be received in an essentially complementary housing provided in the bottom of the other part.

4. Ring according to claim 3, wherein the projecting shape of each of the branches (12a, 12b) of one part is defined by the intersection of a spherical contour (121a, 121b) of one of said branches with an end face (122a, 122b) essentially parallel to an axis of said ring and forming an extension of a semi-cylindrical inner surface (110) defined by the bottom (11) of this same part.

5. Ring according to claim 4, wherein said end face (122a, 122b) of each branch extends obliquely with respect to an axis (XX) of the ring.

6. Ring according to claim 5, wherein the two branches are separated from the bottom by two shoulders (113a, 113b) extending in planes which, with respect to the axis (XX) of the ring, have an obliqueness similar to that of said end faces (122a, 122b).

7. Ring according to claim 1 wherein the branches (12a, 12b) of each part are delimited, on a face facing towards the branches of the other part, by a plane (123a, 123b) perpendicular to the axis of the ring.

8. Ring according to claim 1, wherein the minimum distance (L) between the two branches (12a, 12b) of one same pair is locally shorter than the diameter of a rod (21) intended to take said ring.

9. Osteosynthesis device, for the spine, comprising a bone fixation part which has an essentially spherical seat, a ring housed in said seat, an element for clamping the ring into its seat, and a rod (21) passing through an essentially cylindrical passage formed in the ring, wherein the rod forms part of an element (20) comprising, at the two ends of the rod, two parts (22, 23) which constitute an obstacle to the slipping of a one-piece ring over the rod, and the two parts (10) are fitted onto the rod from the side thereof.

* * * * *